(12) United States Patent
Ruiz Ballesteros et al.

(10) Patent No.: US 8,498,524 B2
(45) Date of Patent: Jul. 30, 2013

(54) VAPORIZER DEVICE OF MULTI-FRAGRANCE VOLATILE SUBSTANCES

(75) Inventors: Julio C Ruiz Ballesteros, Cerdanyola del Valles (ES); Jose A Munoz Martinez, Cerdanyola del Valles (ES); Cedric Morhain, Cerdanyola del Valles (ES); Ruben Garcia Fabrega, Cerdanyola del Valles (ES); Jordi Farre Albaladejo, Cerdanyola del Valles (ES); Andrea Caserta, Cerdanyola del Valles (ES)

(73) Assignee: Zobele Espana, S.A., Barcelona (ES)

( * ) Notice: Subject to any disclaimer, the term of this patent is extended or adjusted under 35 U.S.C. 154(b) by 2212 days.

(21) Appl. No.: 11/117,176

(22) Filed: Apr. 28, 2005

(65) Prior Publication Data

US 2006/0193611 A1    Aug. 31, 2006

(30) Foreign Application Priority Data

Feb. 3, 2005  (WO) ............... PCT/ES2005/000047

(51) Int. Cl.
  *F24F 6/00*  (2006.01)
  *F24F 6/08*  (2006.01)
  *A61L 9/02*  (2006.01)

(52) U.S. Cl.
  USPC ...................... 392/394; 392/395; 239/43

(58) Field of Classification Search
  USPC ... 392/386–406; 428/34.2–36.92; 239/34–60; 122/366
  See application file for complete search history.

(56) References Cited

U.S. PATENT DOCUMENTS

| | | | |
|---|---|---|---|
| 3,974,472 A * | 8/1976 | Gould, Jr. | 345/211 |
| 4,634,614 A * | 1/1987 | Holzner | 428/34.2 |
| 4,782,215 A * | 11/1988 | Kadwell et al. | 219/494 |
| 5,197,375 A * | 3/1993 | Rosenbrock et al. | 99/328 |
| 6,145,241 A * | 11/2000 | Okuno | 43/129 |
| 6,487,367 B2 | 11/2002 | Vieira | |
| 6,501,906 B2 | 12/2002 | Vieira | |
| 6,581,915 B2 | 6/2003 | Bartsch et al. | |
| 6,909,840 B2 * | 6/2005 | Harwig et al. | 392/405 |
| 7,069,090 B2 * | 6/2006 | Huffington et al. | 700/45 |

(Continued)

FOREIGN PATENT DOCUMENTS

| | | |
|---|---|---|
| EP | 0 722 742 A2 | 7/1996 |
| EP | A-1247447 | 10/2002 |
| JP | A-2003-123036 A | 4/2003 |
| WO | WO 01/05442 A1 | 1/2001 |
| WO | WO 2004/080496 A1 | 9/2004 |

*Primary Examiner* — Sang Paik
(74) *Attorney, Agent, or Firm* — Ostrolenk Faber LLP

(57) ABSTRACT

A vaporizer device of the type which is connected to the electric mains by a plug (1), incorporating a single container (6) equipped with a body of two or more independent receptacles (8) which hold different liquid fragrances in which respective wicks (2) are immersed and a lid (9) which closes the body (7) and renders the receptacles (8) independent. The lid (9) comes with openings (10) in correspondence with the positions of the wicks (2) for the egress and vaporization of the fragrance by actuation of one or more resistance elements (3), located in opposition to the openings (10), either with use of a manual pushbutton (4) or automatically in accordance with a pre-established program, diffusing the fragrances in a sequential or combined manner during predetermined intervals of time.

17 Claims, 10 Drawing Sheets

U.S. PATENT DOCUMENTS

| | | |
|---|---|---|
| 2002/0076214 A1 | 6/2002 | Vieira |
| 2002/0146242 A1 | 10/2002 | Vieira |
| 2004/0007787 A1 | 1/2004 | Kvietok |
| 2004/0033171 A1 | 2/2004 | Kvietok et al. |
| 2004/0076410 A1* | 4/2004 | Zobele et al. .................. 392/390 |
| 2004/0247301 A1 | 12/2004 | Yip et al. |
| 2005/0001337 A1* | 1/2005 | Pankhurst et al. ............ 261/104 |

* cited by examiner

VAPORIZER DEVICE OF MULTI-FRAGRANCE VOLATILE SUBSTANCES

OBJECT OF THE INVENTION

The present invention relates to a vaporizer device of multi-fragrance volatile substances of the type of those which are connected to the electricity mains to emit several fragrances sequentially or simultaneously by manual actuation or according to an established program.

An object of the invention is that the container which holds the fragrances is obtained as a compact unit which incorporates in origin compatible fragrances for their possible combined vaporization, obviating the possibility of substituting one of the fragrances with another not compatible with the previous ones.

BACKGROUND OF THE INVENTION

Electric vaporizer devices of volatile substances are known which evaporate perfumes or insecticides into the atmosphere of the type of those which adapt to domestic electric power sockets, have a container of the volatile substance, a resistive heating element, and also a light-emitting means and elements for activation by manual or automatic operation with an associated electronic circuit.

The container of the volatile, generally liquid substance, incorporates a capillary element which transfers the substance from the container to the area in which the heater element is situated which evaporates the substance into the surroundings.

When the container is emptied or when the consumer wishes to use another liquid the container has to be replaced with another new one. The continued use of the same container from which the same liquid odorant is evaporated signifies that with time the user finds his/her perception thereof diminished until reaching olfactory saturation.

The habitual consumer of this type of odorant generally uses a single container until it is exhausted for which reason, during the useful life thereof, only one odour is perceived.

The Patent of Invention WO 01/05442 relates to a fragrance-emitting device which envisages the incorporation of two different fragrances, one is supplied continually and the other periodically so as to interact with the first and prevent the consumer from becoming accustomed to and perceiving a diminution in the intensity of the first fragrance.

The Patent of Invention US 04/0033171 proposes a method to evaporate two or more substances in determined sequences, however it does not resolve the possibility that the user can manipulate the device replacing the containers and therefore the fragrances, combining fragrances that can give rise to a disagreeable result.

On the other hand the Patent of Invention US 2004/0007787 presents a rotary device which has a cartridge with several volatile substances which rotates to evaporate one substance or another in an independent manner, not admitting the combination thereof.

When constituting a perfume the perfume-maker has a broad range of olfactory notes available grouped into families: rustic, aldehydes, musk, woody, balsam, citrus, aniseed, spicy, floral, fruity, mentholated, sweet grass, ozone, vetiver, conifers, tobacco, etc.

Perfumes are likewise composed by three large groupings of olfactory notes: top note, middle note and base note. The top note is that which lasts least and loses its intensity after one hour, the middle note is not so light and loses its intensity after 3 hours and the base note can last up to 24 hours. The correct selection of the ratio between these odours, as well as their concentration, compose and characterize each of the fragrances, making it possible to mark their individual character: fresh, marine, grassy, fruity, oriental, woody, etc.

The possibility of evaporating several fragrances separately or combinations thereof in different concentrations could give rise to different possible configurations that could be used by the perfume-maker to avoid saturation, to freshen the environment with a modulable system or to create an actual fragrance based on its separate components. However the combination of the fragrances in an appropriate manner is specially important for obtaining a satisfactory result.

In the case of the described patents which combine fragrances, these are prepared in independent containers, which can be manipulated and changed by others with fragrances that may not be compatible with the originals, not just from the point of view of olfactory quality but even producing a combination of substances which proves disagreeable.

DESCRIPTION OF THE INVENTION

The vaporizer device of multi-fragrance active substances which constitutes the object of this invention allows olfactory saturation to be suppressed according to a sequence, with the objective of transmitting to the user the perception of the fragrance evolving by simulating what happens with some perfumes the olfactory note of which gradually evolves over the course of time, be this for example the perfumery products applied on the skin, or the natural fragrances secreted by plants into the atmosphere.

The device envisages the incorporation of a single container which has a number of receptacles which contain different fragrances, consisting of volatile substances having harmonious or complementary olfactory notes. The manufacture of a single container with capacity to hold several fragrances results in a simplicity in obtaining the same, and also permits a combination of related fragrances to be supplied in origin without the possibility of substituting one of the fragrances or combining them with others. In the event of wishing to diffuse other combinations of fragrances the container will have to be changed for another which holds other fragrances in its receptacles.

The device has the same number of resistance elements as the number of receptacles and they are supplied with a variable voltage and act by heating each receptacle in accordance with a cycle regulated by a controller, and there are also light-emitting diodes associated with the actuation of each of said resistance elements which inform the user of the liquid or liquids that are being vaporized at any given moment.

By means of this device it is possible to have the same fragrance in three receptacles with different top, middle and base notes, the modulated combined or independent vaporization of the three compositions determining subtle changes in perception, and avoiding the user becoming habituated thereto. Likewise the character of the final fragrance could be modulated or changed by modifying the type and intensity of the fragrances of each recipient.

The device can work in manual or in automatic mode.

In automatic mode the device is programmed in the controller of the electronic circuit, which will connect the different resistance elements in a cyclic manner according to an operating sequence, using either identical operating cycles, or having different durations in terms of the fragrances to be combined, obtaining a variable olfactory intensity as a function of the vaporization temperature which the controller delivers to each of the resistance elements with different effective voltages through power switches.

The operating sequence is programmed so that the consumption of the different fragrances is identical and the duration of each of them is the same so that one fragrance does not finish before another.

The automatic operating mode works indefinitely if the power supply is not interrupted. At any moment the user can activate the manual operating mode or halt the operation of the vaporizer device.

In the manual operating mode, the actuation of a pushbutton one or more times defines the selection of different operating modes, which in all cases will have a determined duration to avoid the excessive consumption of a given fragrance, as well as excessive imbalance in the consumption of fragrances and the olfactory habituation that could occur if the same fragrance were diffused uninterruptedly. Therefore the manual operation of the device has a limited duration, defined for example by a timer. When the operating time has concluded in manual mode, it would pass directly to operation in automatic mode.

In a possible solution the connection of the device to the mains would signify actuation in automatic mode in accordance with the programmed sequence, the first depression of the pushbutton would produce the vaporization of the fragrance contained in a first receptacle during one cycle, a second depression could activate the vaporization of a second fragrance during one cycle, a third depression would activate the vaporization of a third fragrance during one cycle, a fourth depression could interrupt the operation of the device and a fifth depression would return the device to automatic mode. Each of the depressions would define the activation of the light-emitting indicator corresponding to the fragrance that is being diffused.

In the event of accidental interruption of the power supplied, an EEPROM type auxiliary memory is foreseen in the electronic controller which allows, on restoring the consumption, the device to restart in the same operating mode in which the cycle was when the incident took place.

As an option the possibility is contemplated of increasing the olfactory intensity, both if the system is working in manual mode and in automatic mode, by the incorporation of a potentiometer regulated by a rotary control on which the user acts. This potentiometer is connected to the electronic circuit and sends a signal to the controller so that the latter increases the effective voltage across the resistance elements, which signifies an increase in the temperature of the resistance elements which results in an increase in vaporization rate and therefore in a greater vaporization of the fragrances into the atmosphere.

Also it has been foreseen optionally that for a container which incorporates a specific combination of fragrances, the same has an encoded board associated with a series of specific parameters of vaporization, such as vaporization temperature, operating sequence and duration of the cycles, in correspondence with a sensor mounted in the electronic circuit, which reads those parameters from the board, transmits them to the controller and triggers the operation of the vaporizer device.

The multi-fragrance container comprises a body equipped with transparent receptacles to allow viewing the levels of the different fragrances stored in each receptacle, and also in each receptacle there can be lenses which can display colours in accordance with the fragrance, the location of which immediately below the diodes allows the fragrance to be indicated which is being diffused when it is illuminated by the diodes. Thus for example pink can indicate that the odour is of raspberry, rose or pomegranate, red can refer to sequoia wood or vanilla and orange can indicate amber, wood and Mediterranean spices. In this way the user can perceive and more easily remember the different olfactory events which he is perceiving.

The container is conceived therefore as a single body which reduces the number of components considerably, is manufactured by known processes such as injection of plastic or thermoforming, is filled in the horizontal position and is rotated through 90° into its operative vertical position.

Additionally the container comprises parallel capillary wicks which fit in the receptacles and over said wicks is located a plastic cover which is welded to the body and which comes with some openings, one in correspondence with each wick, which are covered by means of a multilayer seal which seals the container until its use by the consumer. The wicks can be of paper or the like and have on one of their faces, images, information or colours which enable the user to recognize the evaporated fragrance.

This seal is formed by several layers: an outer layer of plastic or metallic material which provides mechanical consistency and allows the printing thereon of the information necessary for the consumer concerning how it should be removed for use, an intermediate layer of plastic or metallic material which serves as a barrier to prevent the vaporization of undesired fragrances and an inner layer of plastic material in contact with the lid which covers the openings to prevent the liquid contained in the receptacles from leaking.

The union between the seal and the lid is established by fusion of the plastic materials of both, either by applying pressure and heat (thermowelding) or by applying pressure and vibration (ultrasonics). The seal can be prolonged laterally in individual tabs which project with respect to the lid at both sides to enable the gripping thereof to tear off the seal.

The device has a casing formed by two halves, a front one and a rear one joined by means of mechanical engagement between which the electronic circuit board is held, a piece which supports and guides the connection plug which supplies power to the electronic circuit and an intermediate insulating piece which acts as guide for the correct insertion of the container, having likewise means of engagement between the container and the casing.

On one of the halves of the casing a screen is defined through which the fragrance is diffused to the surroundings.

DESCRIPTION OF THE DRAWINGS

To complete the description that is being made and with the object of assisting in a better understanding of the characteristics of the invention, in accordance with a preferred practical embodiment thereof, as an integral part of said description, the same is accompanied with a set of drawings wherein, by way of illustration and not restrictively, the following has been represented.

PREFERRED EMBODIMENT OF THE INVENTION

Figure 1:
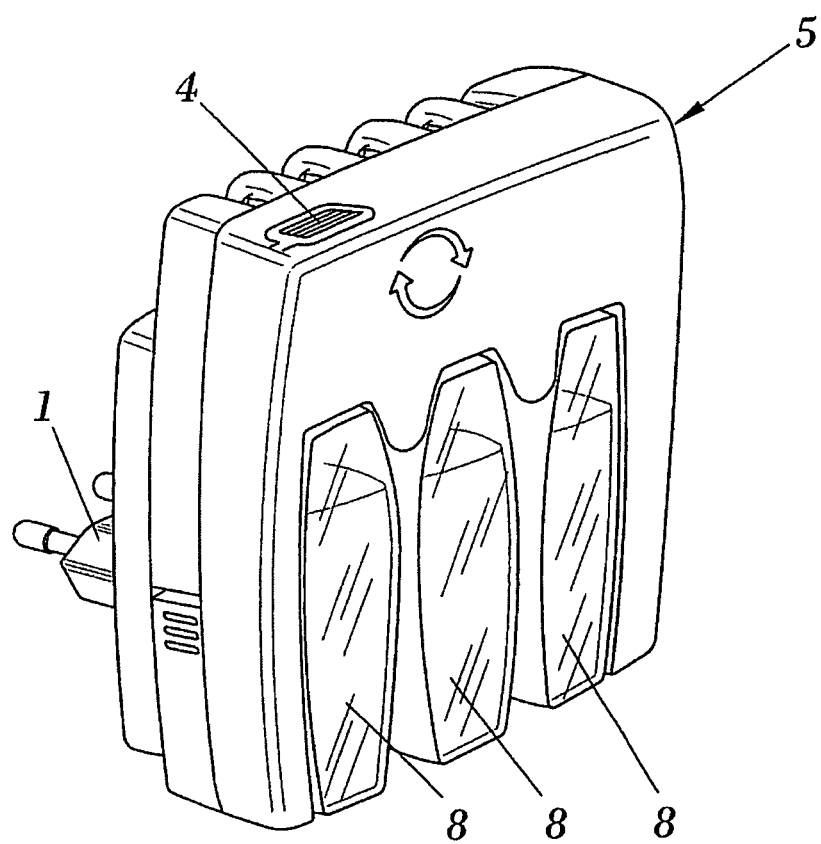
FIG. 1—It shows a view in perspective of the multi-fragrance volatile substance vaporizer device.

The vaporizer device of multi-fragrance volatile substances which constitutes the object of this invention is of the type of those which are connected to the electric mains by means of a plug (1), incorporate two or more liquid fragrances in which respective wicks (2) are immersed and which have two or more resistance elements (3) located in correspondence with the wicks (2), which when activated, by means of a manual pushbutton (4) or automatically in accordance with a pre-established program, emit the fragrances in a sequential or combined manner during predetermined intervals of time through a casing (5).

Figure 4:
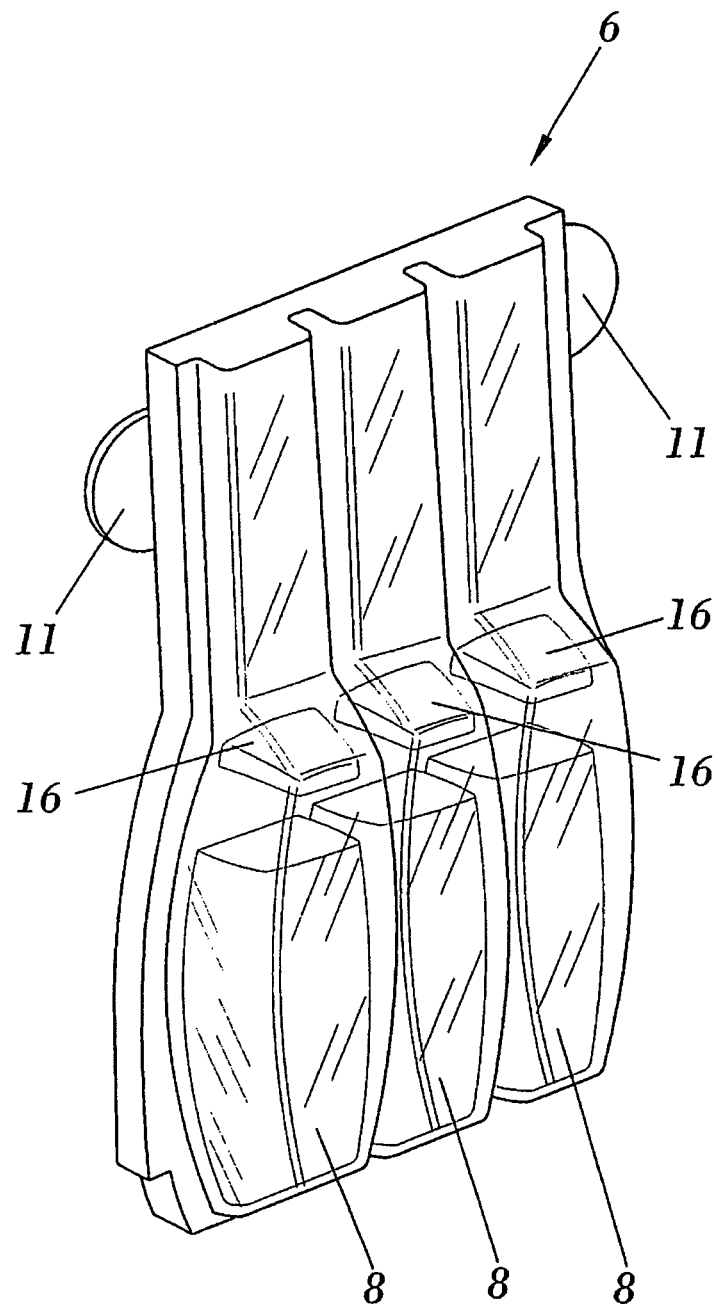
FIG. 4—It shows a view in perspective of the container.
Figure 5:
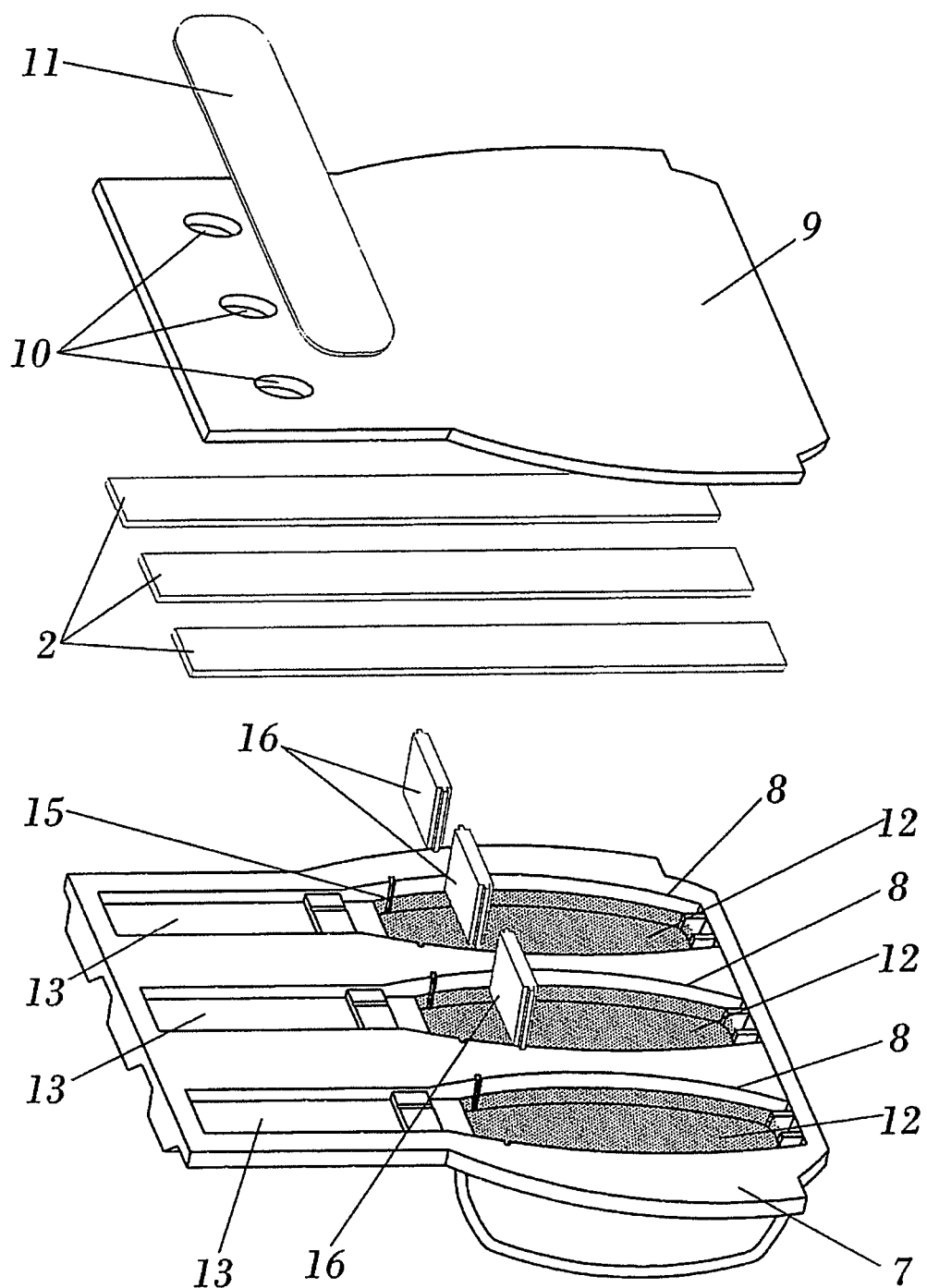
FIG. 5—It shows an exploded view of the constituent elements of the container.

The vaporizer device is distinguished fundamentally because it incorporates a single container (6) represented in FIG. 4, which comprises a body (7), preferably transparent, equipped with two or more independent receptacles (8) which hold the different fragrances, such as is observed in FIG. 5, as well as two or more wicks (2), each housed in a receptacle (8), a lid (9) which seals the body (7) and renders the receptacles (8) independent which comes with openings (10) in correspondence with the positions of the wicks (2) for the egress and vaporization of the fragrance by activation of the respective resistance elements (3) located in opposition to said openings (10), and a seal (11) which covers the openings (10) in the non-operative condition of the vaporizer device.

Each of the receptacles (8) comprises a cavity (12) which contains the fragrance from which projects with less height a planar housing (13) which holds a wick (2) which is prolonged into the cavity (12).

Figure 2:
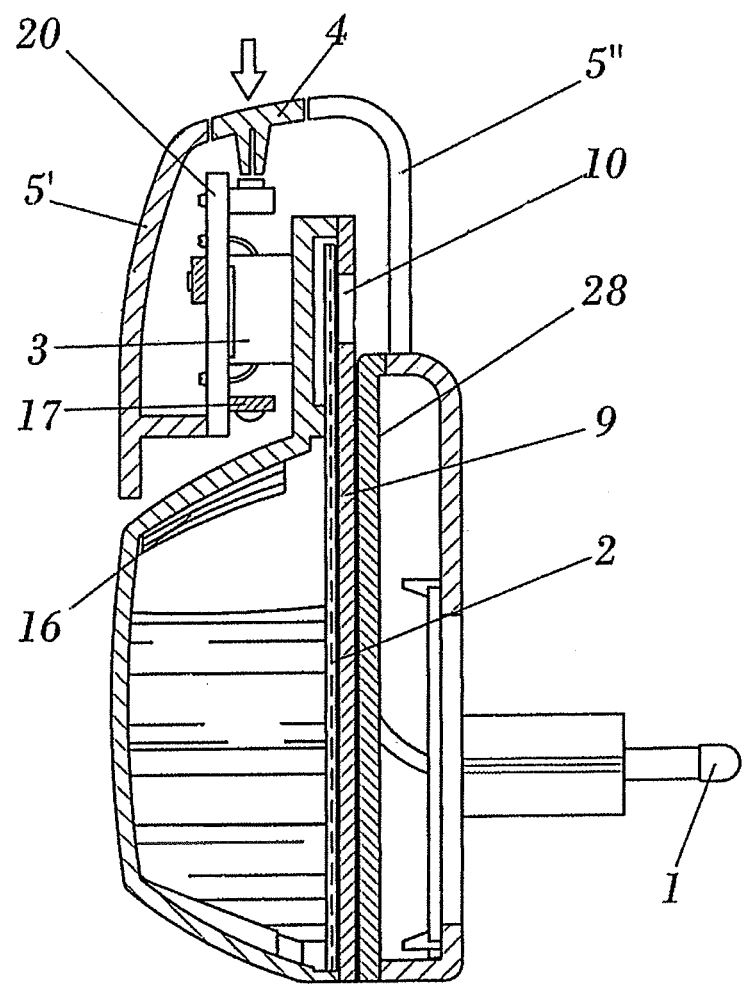
FIG. 2—It shows a side view in cross-section of the multi-fragrance vaporizer device.

The possibility has been foreseen in the cavities (12) that some guides (15) are defined on which an indicator lens (16) is fitted, in correspondence with each of which there is a light-emitting diode (17) which illuminates the indicator lens (16), represented in FIG. 2, as a signal indicating the vaporization of the fragrance contained in said cavity (12) by actuation of the corresponding resistance element (3).

Furthermore, it is pointed out that the seal (11) which covers the openings (10) extends laterally on both sides of the lid (9) in individual tabs which enable it to be grasped, such as is appreciated in FIG. 4. Also the seal (11) is configured by means of an inner layer which prevent leakage, an intermediate layer functioning as a barrier to the vapours of the fragrances and an outer layer intended for printing legends.

Figure 3:
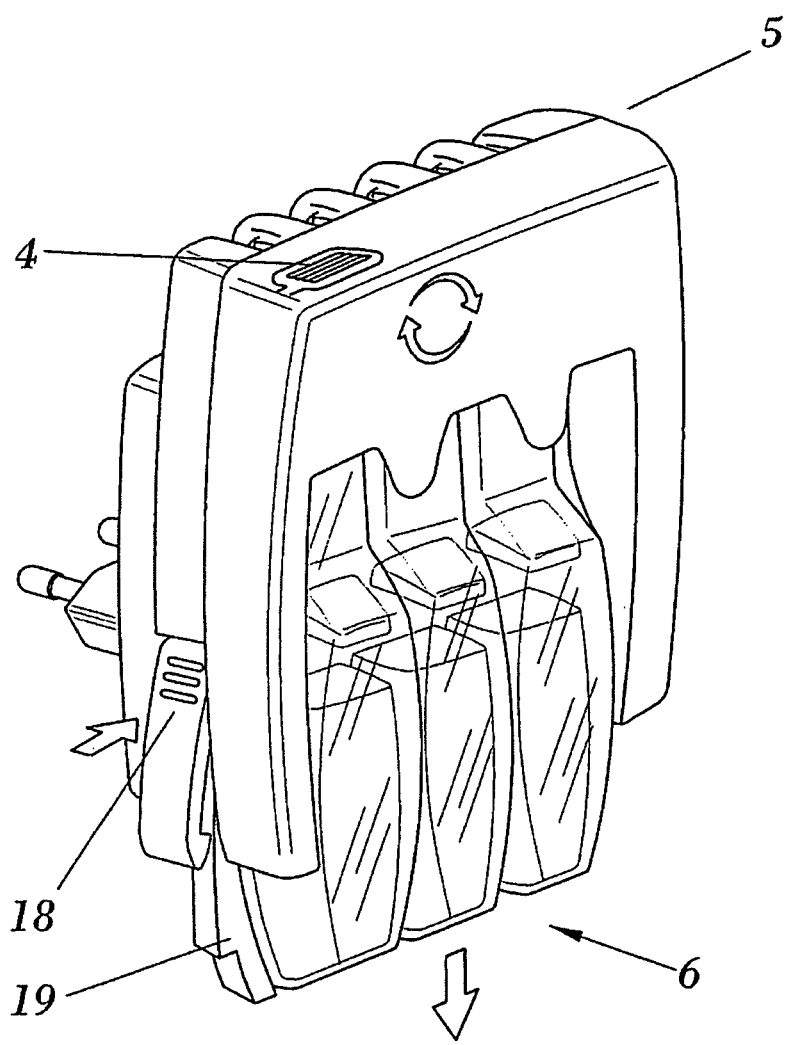
FIG. 3—It shows a view in perspective of the extraction phase of the container downwards.

Such as is observed in FIG. 3, it has been foreseen that the casing (5) has means for engagement (18) and that the body (7) of the container (6) has some lateral projections (19) on which said means of engagement (18) are anchored in order to establish the connection between casing (5) and container (6).

Figure 6:
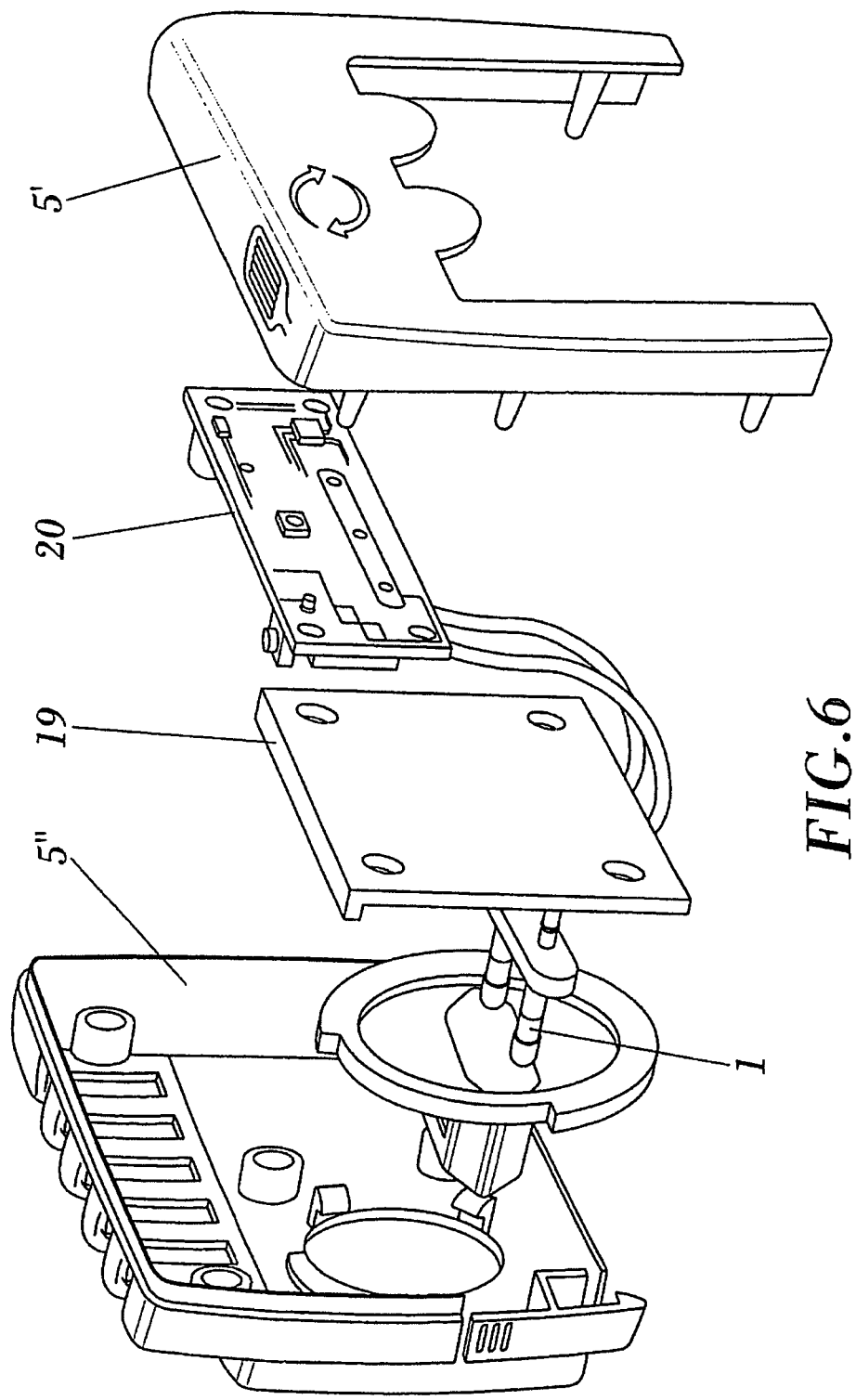
FIG. 6—It shows an exploded view of the constituent elements of the vaporizer device in which the container is not shown.

The casing (5) can be constituted by two halves (5', 5") between which an insulating intermediate plate (28) is housed, represented in FIGS. 2 and 6, which constitutes an element for guidance and support of the container (6).

Inside the casing (5) the mounting is envisaged of a printed circuit (20) which incorporates the resistance elements (3), a programmable controller which controls the sequence of actuation of the resistance elements (3), the simultaneity thereof and the time of vaporization, as well as additionally it can have an EEPROM memory which allows the sequence of fragrance vaporization to be resumed in the event of a cut in the electricity supply. The light-emitting diodes (17) also can be located on said printed circuit (20).

Figure 7:
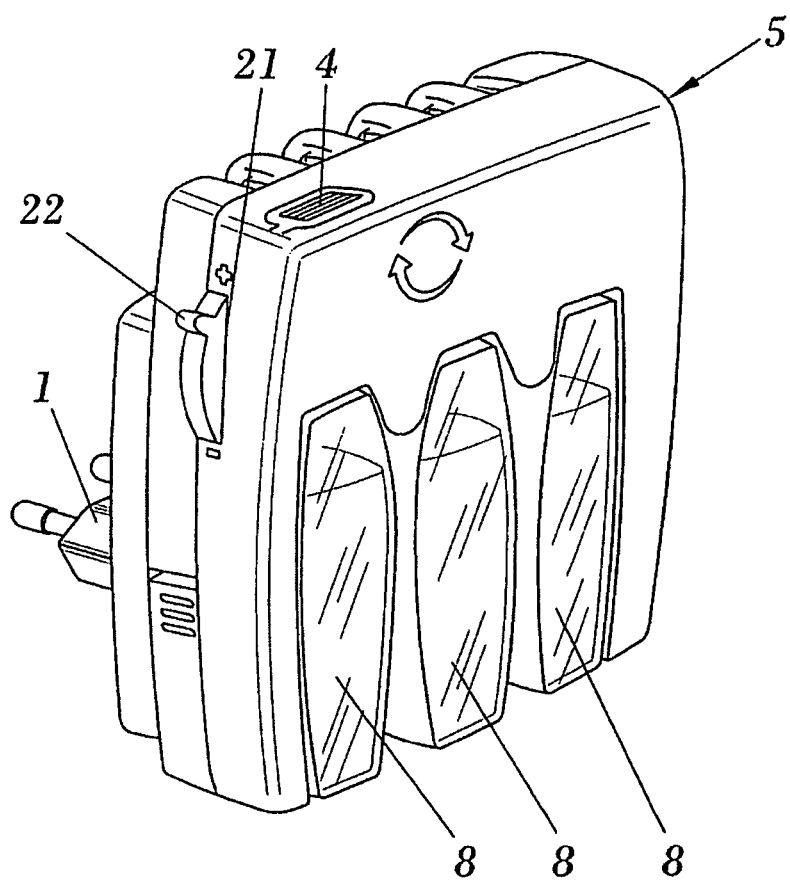
FIG. 7—It shows a view of the vaporizer device for the case of incorporating a potentiometer to regulate the vaporization intensity.
Figure 9:
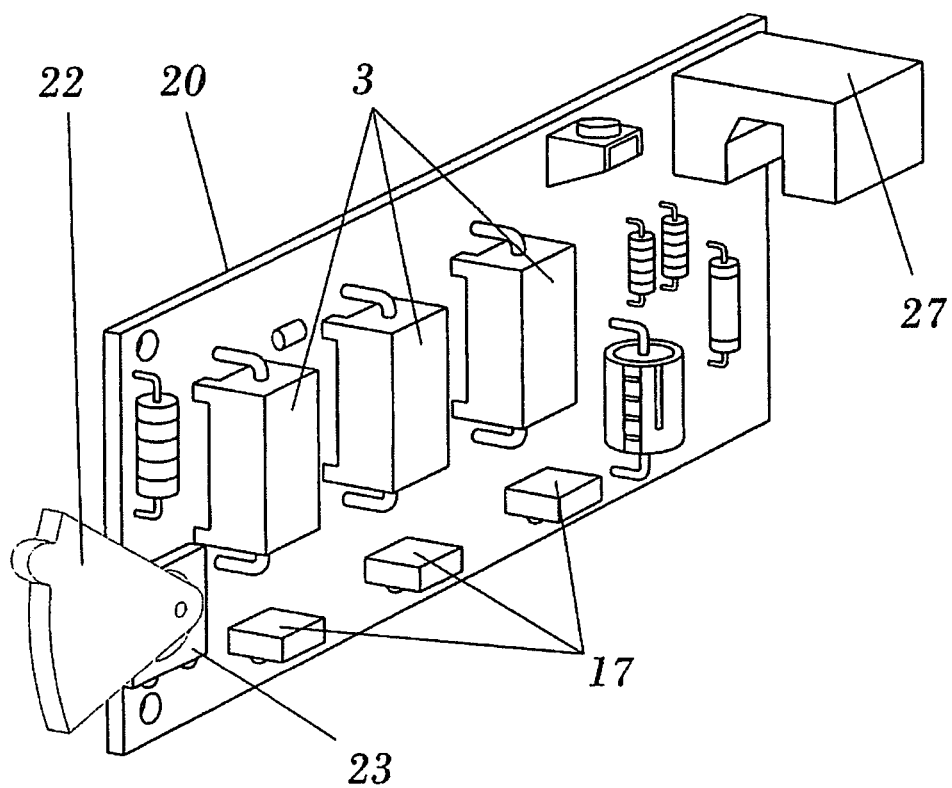
FIG. 9—It shows a view of the printed circuit in which one can observe the rotary control of the potentiometer, the resistance elements, and also the detector of the encoded board of the container is appreciated.

In a possible embodiment represented in FIG. 7 it is envisaged that the casing (5) has an opening (21) in which is a rotary control (22), adjustable manually by the user which is linked to a potentiometer (23) connected to the printed circuit (20), represented in FIG. 9, which sends a signal to the controller from which the voltage of the resistance elements (3) is regulated determining a variation in their temperature and therefore in the rate of vaporization of the fragrances.

Figure 8:
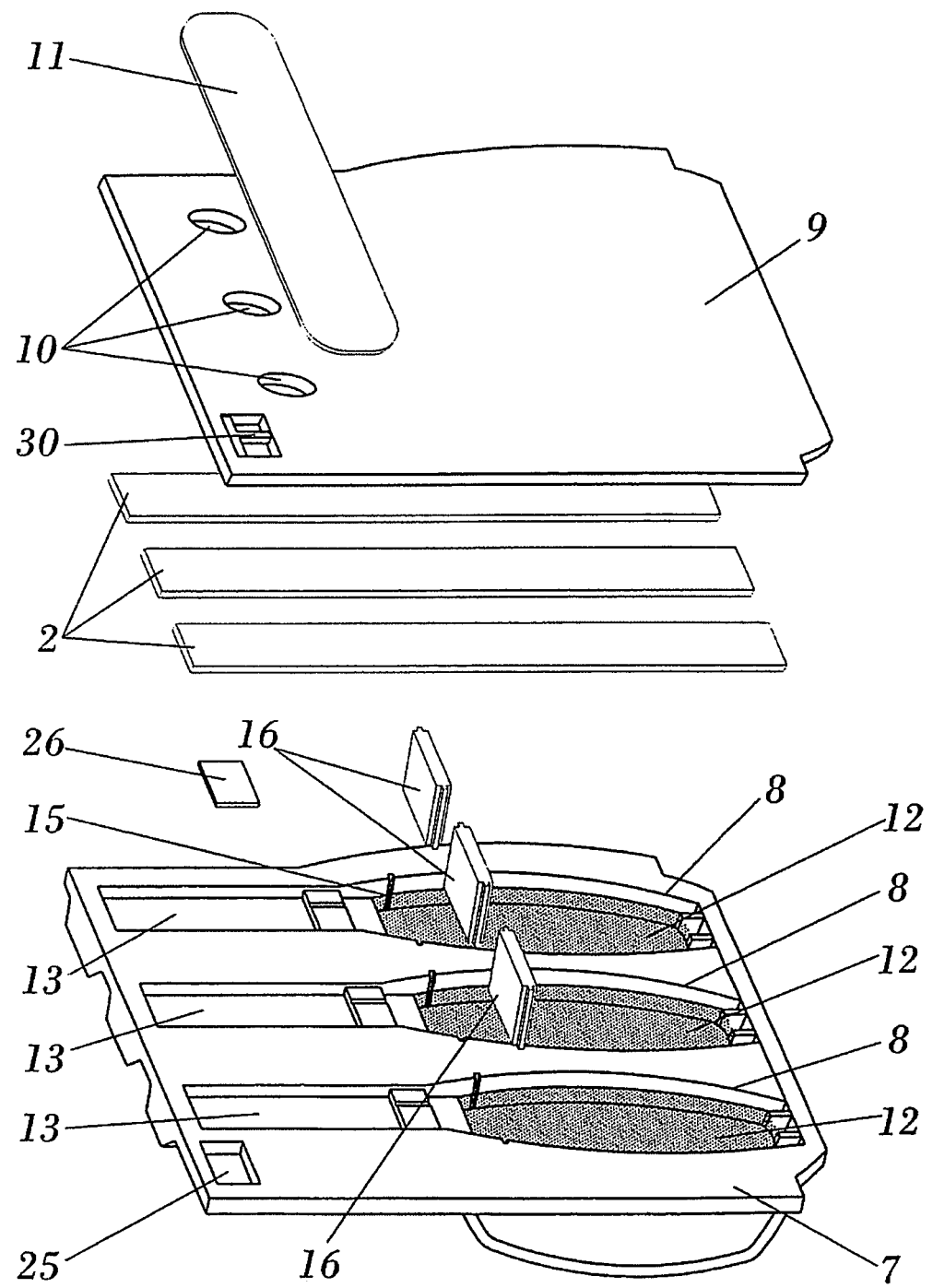
FIG. 8—It shows an exploded view of the container for the solution in which it has an encoded board.

Also it has been foreseen optionally that the container (6) has a housing (25), as is represented in FIG. 8 which holds an encoded board (26) which contains optimum vaporization parameters associated with the combination of fragrances of the container, and that the printed circuit (20) which is shown in FIG. 9, has a detector (27) in correspondence with the encoded board (26) which reads said parameters and transmits them to the controller to trigger the vaporization of fragrances in accordance with said parameters.

Figure 10:
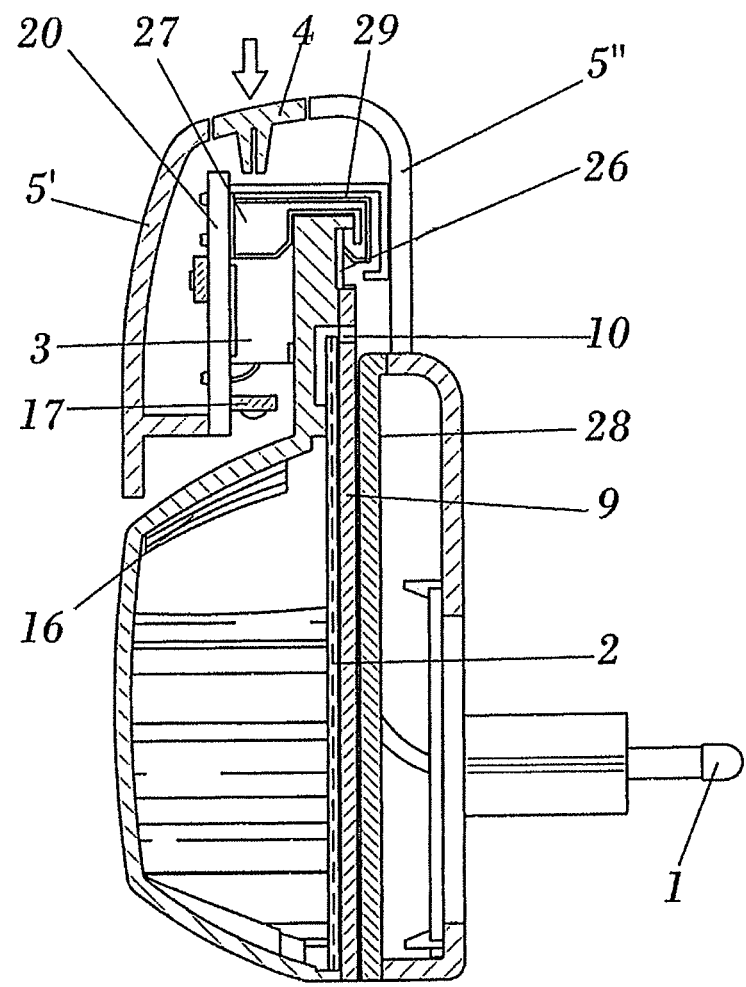
FIG. 10—It shows a view in cross-section of the vaporizer device for the solution of linking the encoded board to the detector by means of electric contacts.

In a possible embodiment, such as is observed in FIG. 8, in correspondence with the encoded board (26) a frame (30) of reduced size is mounted coupled to the lid (9), and from the detector (27) represented in FIG. 10 some electric contacts (29) emerge connected only with the encoded board (26) in those locations of the same in correspondence with the sectors where the frame (30) passes.

The invention claimed is:

1. Vaporizer device of multi-fragrance volatile substances, of the type of those which are connected to the electric mains by means of a plug (1), of those which incorporate two or more liquid fragrances in which respective wicks (2) are immersed and have two or more resistance elements (3) located in correspondence with the wicks (2) which when actuated, by means of a manual pushbutton (4) or automatically in accordance with a pre-established program, diffuse the fragrances in a sequential or combined manner during predetermined intervals of time through a casing (5), wherein it incorporates a single container (6) which comprises:

a body (7) equipped with two or more independent receptacles (8) which hold the different fragrances, two or more wicks (2), each one housed in a receptacle (8), a lid (9) which seals the body (7) and renders the receptacles (8) independent which comes with openings (10) in correspondence with the positions of the wicks (2) for the egress and vaporization of the fragrance by actuation of the respective resistance elements (3) located in opposition to said openings (10), and a seal (11) which covers the openings (10) in the non-operative situation of the vaporizer device, wherein, inside the casing (5) a printed circuit board (20) is mounted which incorporates the resistance elements (3) and a programmable controller which controls the sequence of actuation of the resistance elements (3);

and wherein container (6) has a housing (25) which holds an encoded board (26) which contains vaporization parameters associated with the combination of fragrances of the container, and the printed circuit board (20) has a detector (27) in correspondence with the encoded board (26) which reads said parameters and transmits them to the controller to trigger the vaporization of fragrances in accordance with said parameters.

2. Vaporizer device of multi-fragrance volatile substances according to claim 1, wherein each of the receptacles (8) comprises a cavity (12) which contains the fragrance from which a planar housing (13) of less height projects which houses a wick (2) which is prolonged into the cavity (12).

3. Vaporizer device of multi-fragrance volatile substances according to claim 2, wherein in the cavities (12) some guides (15) are defined on which an indicator lens (16) is fitted, in correspondence with each of which there is a light-emitting diode (17) which illuminates the indicator lens (16) when the corresponding resistance element (3) is actuated, reflecting the colour corresponding to the fragrance contained in said cavity (12) as a signal indicating the vaporization of the same.

4. Vaporizer device of multi-fragrance volatile substances according to claim 1, wherein the casing (5) has means of engagement (18) and the body (7) of the container (6) has some lateral projections (19) on which said means of engagement (18) are anchored to establish the connection between casing (5) and container (6).

5. Vaporizer device of multi-fragrance volatile substances according to claim 4, wherein the casing (5) is constituted by two halves (5', 5") between which an insulating plate (28) is held which constitutes an element of guidance and support of the container (6).

6. Vaporizer device of multi-fragrance volatile substances according to claim 1, wherein the printed circuit (20) has an EEPROM memory which allows the sequence of the fragrance vaporization to be resumed in the event of a cut in the electricity supply.

7. Vaporizer device of multi-fragrance volatile substances according to claim 3, wherein inside the casing (5) a printed circuit (20) is mounted which incorporates the resistance elements (3) and a programmable controller which controls the sequence of actuation of the resistance elements (3), the light-emitting diodes (17) are located on the printed circuit (20).

8. Vaporizer device of multi-fragrance volatile substances according to claim 1, wherein the seal (11) which covers the openings (10) extends laterally on both sides of the lid (9) in individual tabs which enable it to be grasped.

9. Vaporizer device of multi-fragrance volatile substances according to claim 8, wherein the seal (11) is configured by means of an inner layer which prevents leaks, an intermediate layer functioning as a barrier to the vapours of the fragrances and an outer layer intended for printing legends.

10. Vaporizer device of multi-fragrance volatile substances according to claim 1, wherein the printed circuit (20) incorporates a timer connected to the controller which limits the time of manual vaporization after which it passes directly to automatic functioning.

11. Vaporizer device of multi-fragrance volatile substances according to claim 1, wherein the casing (5) has an opening (21) in which there is a rotary control (22), adjustable manually by the user which is linked to a potentiometer (23) connected to the printed circuit (20) which sends a signal to the controller from which the voltage of the resistance elements (3) is regulated determining a variation in their temperature and therefore in the rate of vaporization of the fragrances.

12. Container of multi-fragrance volatile substances, comprising:
   a body (7) equipped with two or more independent receptacles (8) which hold the different fragrances,
   two or more wicks (2), each one housed in a receptacle (8),
   a lid (9) which closes the body (7) and renders the receptacles (8) independent which comes with openings (10) in correspondence with the positions of the wicks (2) for the egress and vaporization of the fragrance by actuation of the respective resistance elements (3) located in opposition to said openings (10),
   a seal (11) which covers the openings (10) in the non-operative condition of the vaporizer device; and
   a housing (25) which holds an encoded board (26) which contains vaporization parameters associated with the combination of fragrances of the container (6).

13. Container of multi-fragrance volatile substances according to claim 12, wherein each of the receptacles (8) comprises a cavity (12) which contains the fragrance from which a planar housing (13) projects at less height which holds a wick (2) that is prolonged into the cavity (12).

14. Container of multi-fragrance volatile substances according to claim 13, wherein in the cavities (12) some guides (15) are defined on which an indicator lens (16) is fitted associated with the activation of the fragrance.

15. Container of multi-fragrance volatile substances according to claim 12, wherein the body (7) of the container (6) has some lateral projections (19) for engagement.

16. Container of multi-fragrance volatile substances according to claim 12, wherein the seal (11) which covers the openings (10) extends laterally on both sides of the lid (9) in individual tabs which enable the grasping thereof.

17. Container of multi-fragrance volatile substances according to claim 16, wherein the seal (11) is configured by means of an inner layer which prevents leakage, an intermediate layer functioning as a barrier to the vapours of the fragrances and an outer layer intended for printing legends.

* * * * *